United States Patent [19]

Borghard et al.

[11] Patent Number: 5,264,641

[45] Date of Patent: Nov. 23, 1993

[54] AROMATICS SATURATION WITH CATALYSTS COMPRISING CRYSTALLINE ULTRA-LARGE PORE OXIDE MATERIALS

[75] Inventors: William S. Borghard, Yardley, Pa.; Cynthia T. Chu, Princeton, N.J.; Thomas F. Degnan, Moorestown, N.J.; Stuart S. Shih, Cherry Hill, N.J.

[73] Assignee: Mobil Oil Corp., Fairfax, Va.

[21] Appl. No.: 989,860

[22] Filed: Dec. 14, 1992

[51] Int. Cl.⁵ .............................................. C07C 5/10
[52] U.S. Cl. .................................. 585/269; 585/266; 585/271; 585/273
[58] Field of Search .............. 585/266, 273, 275, 276, 585/269, 270

[56] References Cited

U.S. PATENT DOCUMENTS 3,197,398 7/1965 Young ................................. 208/111
4,087,353 5/1978 Rausch ............................... 208/143
4,859,648 8/1989 Landis et al. ....................... 502/242
5,057,296 10/1991 Beck ................................... 423/277
5,098,684 3/1992 Kresge et al. ...................... 423/277
5,102,643 4/1992 Kresge et al. ...................... 423/328

FOREIGN PATENT DOCUMENTS 1795668 2/1973 Fed. Rep. of Germany .

Primary Examiner—Asok Pal
Assistant Examiner—P. Achutamurthy
Attorney, Agent, or Firm—Alexander J. McKillop; Dennis P. Santini; Edward F. Kenehan, Jr.

[57] ABSTRACT

There is provided a method for hydrogenating aromatics with a catalyst comprising a crystalline ultra-large pore oxide material. The catalyst also comprises a hydrogenation metal, such as palladium. The process may be used to saturate benzene to form cyclohexane.

16 Claims, No Drawings

AROMATICS SATURATION WITH CATALYSTS COMPRISING CRYSTALLINE ULTRA-LARGE PORE OXIDE MATERIALS

BACKGROUND

There is provided a process for hydrogenating aromatics with a catalyst comprising a crystalline ultra-large pore oxide material. The catalyst also comprises a hydrogenation metal.

LIQUID CRYSTALS, AMPHIPHILES, MICELLES, LYOTROPIC PHASES

Amphiphilic compounds, also referred to as amphiphiles, surface-active agents or surfactants, are composed of molecules which contain both at least one polar or hydrophilic "head" group and at least one non-polar or hydrophobic "tail". In aqueous solution, amphiphilic compounds may associate with each other to form structures known as micelles. These micelles are most often spherical structures in which the polar head groups form the outer surface and the non-polar tails form the inner portion or core of the sphere. Micelles are stable colloidal aggregates which are formed by amphiphiles above a specific concentration, which is called the critical micelle concentration or "CMC". Amphiphiles often have the further ability to arrange into various other, energetically favorable, ordered structures (e.g., liquid crystalline phases) in solution in response to certain stimuli. These stimuli include concentration of the amphiphile, temperature, pressure, ionic composition of solution, presence of organic or inorganic species in solution, etc.

The head group of an amphiphile may bear a positive or negative charge. Anionic amphiphilic compounds have a hydrophilic head group which bears a negative charge; a typical anionic amphiphilic compound is R—O—SO$_3$—, in which R represents a hydrocarbon chain, the hydrophobic "tail" group. The negative charge associated with the anionic head group is usually balanced by a small cation, such as H+, Na+, K+ or NH$_4$+. Cationic amphiphilic compounds have a hydrophilic head group which bears a positive charge; a typical cationic amphiphilic compound is R(CH$_3$)$_3$N+ where R again represents a hydrocarbon chain (the tail group). The positive charge associated with the cationic head group is usually balanced by a small anion, such as OH—, Cl—, Br—or SO$_4$=. The length of the chain (R) is critical to the function of an amphiphilic species, as, in aqueous solution, hydrocarbon chain lengths below 6 carbons do not energetically favor aggregation to form micellar phases, and carbon chain lengths above 36 carbons do not exhibit sufficient solubility to achieve CMC status. There exist other amphiphilic compounds, some bearing no net charge, that produce liquid crystal phases in solution. These include the general classes of nonionic and zwitterionic surfactants. An exhaustive review of this chemistry is found in a review article by Winsor (*Chemical Reviews*, 68, 1, (1968)).

Liquid crystals are materials which exhibit aspects of both the crystalline solid and amorphous liquid state. They resemble liquids in their ability to flow, and solids in the degree of order within their structure. In many systems, this order is established spontaneously. In other cases, it can be brought about, or controlled, by electric, magnetic, or hydrodynamic fields. Lyotropic liquid crystals comprise a large body of known liquid crystalline systems. These lyotropic systems are often comprised of two components: a solvent (e.g, water) and an amphiphilic compound. In many cases, however, additional components such as salts or other inorganic or organic compounds may be present in a lyotropic system. Such solvent-containing systems are often referred to as solutions, although it will be understood that such solutions are not true molecular solutions insofar as amphiphilic compounds are present as micellar aggregates as opposed to individual molecular species.

HEXAGONAL, CUBIC AND LAMELLAR PHASES

Liquid crystal/micellar aggregates may exhibit various structures. For example, three well known phases of lyotropic liquid crystals are the hexagonal, cubic and lamellar phases. The presence of these phases in a micellar solution containing amphiphilic compounds will be determined by a large number of factors including the concentration of the amphiphile, the presence of ions, other organic or inorganic molecules, temperature, etc. The existence of such phases in micellar solutions containing amphiphilic species are determined by a variety of techniques including, for example, X-ray diffraction techniques. X-ray diffraction and other studies of the hexagonal phase provide evidence that the amphiphilic species contained therein are arranged into rodlike micelles, or clusters, of indefinite length, and that these rods are stacked in a hexagonal array. e.g., each rod is surrounded by six nearest neighbors. Thus, liquid crystalline medium may be fashioned so as to contain the amphiphilic species packed in a hexagonal array.

Lamellar liquid crystalline phases are distinctly different from hexagonal phases in that the amphiphilic molecules do not form hexagonally packed rods. An example of a lamellar liquid crystalline phase may be thought of in terms of sheets composed of bilayers of amphiphilic molecules separated from each other by intervening water layers. The amphiphilic molecules within each lamella may be oriented perpendicular to the plane of the lamella, or tilted. For comparable surfactants, lamellar phases are usually found at higher surfactant concentration than are hexagonal phases.

Another liquid crystalline phase is the cubic phase. Such phases are sometimes formed at concentrations of amphiphile intermediate between those producing the lamellar phase and the hexagonal phase. Optical observations of the cubic phases only reveal that the structure is isotropic. X-ray diffraction studies have shown that these structures may be characterized as face-centered or body-centered cubic, although the detailed structure remains uncertain. It has often been argued, however, that these structures are bicontinuous. A particular type of cubic phase observed for liquid crystalline phases is known as Ia3d.

MICELLAR SOLUBILIZATION

Liquid crystal systems, in certain of their phases, exhibit properties which may be probed by various experimental means. For example, amphiphilic species which aggregate as micelles exhibit an important property known as micellar solubilization. The ability of micelles to solubilize non-polar organic species and thus "swell" to larger proportions is critically important to an amphiphilic species' role in common detergent formulations. This ability is discussed in detail in the aforementioned review article by Winsor.

SURFACTANT CHAIN LENGTH

A factor concerning the ability of amphiphilic compounds to form micelles is the "Critical Micelle Concentration" or "CMC". The CMC is a measure of the aqueous concentration of surfactant at which micelles first begin to appear. A very extensive tabulation of CMC data has been compiled by Mukerjee and Mysels, "Critical Micelle Concentrations of Aqueous Surfactant Systems", National Standard Data Reference Service, NSDR 50-NBS 36, National Bureau of Standards, USA. Typical CMC's of alkyltrimethylammonium bromide salts range from $10^{-1}$ M to $10^{-2}$ M for $C_6$, $C_8$ salts, to $10^{-4}$ M for $C_{16}$ salts.

It is well known in the surfactant literature that the diameter of micelles is, among other factors, controlled by the chain length of the amphiphilic species from which they are formed. Micelle formation with smaller alkyl chain length quaternaries such as $C_6$, and under most conditions $C_8$, is generally an energetically unfavorable event. The solubilities of these short chain quaternaries are quite high (>50 wt.% in water is achievable) and micellar structures are not necessary to minimize hydrophobic interactions.

SOLID CRYSTALLINE OXIDES

Zeolites, both natural and synthetic, have been demonstrated in the past to have catalytic properties for various types of hydrocarbon conversion. Certain zeolitic materials are ordered, porous crystalline aluminosilicates having a definite crystalline structure as determined by X-ray diffraction, within which there are a large number of smaller cavities which may be interconnected by a number of still smaller channels or pores. The pore systems of other zeolites lack cavities, and these systems consist essentially of undimensional channels which extend throughout the crystal lattice. Since the dimensions of zeolite pores are such as to accept for adsorption molecules of certain dimensions while rejecting those of larger dimensions, these materials are known as "molecular sieves" and are utilized in a variety of ways to take advantage of these properties.

Such molecular sieves, both natural and synthetic, include a wide variety of positive ion-containing crystalline silicates. These silicates can be described as a rigid three-dimensional framework of $SiO_4$ and, optionally, Periodic Table Group IIIB element oxide, e.g., $AlO_4$, in which the tetrahedra are cross-linked by the sharing of oxygen atoms whereby the ratio of the total Group IIIB element, e.g., aluminum, and Group IVB element, e.g., silicon, atoms to oxygen atoms is 1:2. The electrovalence of the tetrahedra containing the Group IIIB element, e.g., aluminum, is balanced by the inclusion in the crystal of a cation, for example, an alkali metal or an alkaline earth metal cation. This can be expressed wherein the ratio of the Group IIIB element, e.g., aluminum, to the number of various cations, such as Ca/2, Sr/2, Na, K or Li, is equal to unity. One type of cation may be exchanged either entirely or partially with another type of cation utilizing ion exchange techniques in a conventional manner. By means of such cation exchange, it has been possible to vary the properties of a given silicate by suitable selection of the cation. The spaces between the tetrahedra are occupied by molecules of water prior to dehydration.

Prior art techniques have resulted in the formation of a great variety of synthetic zeolites. Many of these zeolites have come to be designated by letter or other convenient symbols, as illustrated by zeolite A (U.S. Pat. No. 2,882,243); zeolite X (U.S. Pat. No. 2,882,244); zeolite Y (U.S. Pat. No. 3,130,007); zeolite ZK-5 (U.S. Pat. No. 3,247,195); zeolite ZK-4 (U.S. Pat. No. 3,314,752); zeolite ZSM-5 (U.S. Pat. No. 3,702,886); zeolite ZSM-11 (U.S. Patent 3,709,979); zeolite ZSM-12 (U.S. Pat. No. 3,832,449); zeolite ZSM-20 (U.S. Pat. No. 3,972,983); ZSM-35 (U.S. Pat. No. 4,016,245); and zeolite ZSM-23 (U.S. Pat. No. 4,076,842), merely to name a few.

The $SiO_2/Al_2O_3$ ratio of a given zeolite is often variable. For example, zeolite X can be synthesized with $SiO_2/Al_2O_3$ ratios of from 2 to 3; zeolite Y, from 3 to about 6. In some zeolites, the upper limit of the $SiO_2/Al_2O_3$ ratio is unbounded. ZSM-5 is one such example wherein the $SiO_2/Al_2O_3$ ratio is at least 5 and up to the limits of present analytical measurement techniques. U.S. Pat. No. 3,941,871 (Re. 29,948) discloses a porous crystalline silicate made from a reaction mixture containing no deliberately added alumina in the recipe and exhibiting the X-ray diffraction pattern characteristic of ZSM-5. U.S. Pat. Nos. 4,061,724; 4,073,865 and 4,104,294 describe crystalline silicates of varying alumina and metal content.

Aluminum phosphates are taught in U.S. Pat. Nos. 4,310,440 and 4,385,994, for example. These aluminum phosphate materials have essentially electroneutral lattices. These lattices may be described in terms of alternating $AlO_4$ and $PO_4$ tetrahedra. An example of such an aluminum phosphate is a material designated as $AlPO_4$-5.

Details of the structure of $AlPO_4$-5 are given by Meier and Olson in *Atlas of Zeolite Structure Types*, 2nd rev. ed. (1987), published on behalf of the Structure Commission of the International Zeolite Association by Butterworths. More particularly, Meier and Olson indicate that $AlPO_4$-5, also designated as AFI, is a material having pore windows formed by 12 tetrahedral members, these windows being about 7.3 Angstroms in diameter.

Of the siliceous zeolites discussed hereinabove, zeolites X and Y have the largest pore diameter and overall pore volume. Zeolites X and Y are synthetic analogues of the naturally occurring zeolite, faujasite. Details of the structure of faujasite are also given by Meier and Olson, ibid. More particularly, Meier and Olson indicate that faujasite, also designated as FAU, is a material having pore windows formed by 12 tetrahedral members, these windows being about 7.4 Angstroms in diameter. For the purposes of the present disclosure, the terms, siliceous zeolite and siliceous oxide, are defined as materials wherein at least 50 mole percent of the oxides thereof, as determined by elemental analysis, are silica. The pore volume of faujasite is believed to be about 0.26 cc/g.

An oxide material with even larger pores than faujasite and $AlPO_4$-5 is a material designated as VPI-5. The structure of VPI-5 is described by Davis et al. in an article entitled, "VPI-5: The first molecular sieve with pores larger than 10 Angstroms", *Zeolites*, 8, 362-366 (1988). As indicated by Davis et al., VPI-5 has pore windows formed by 18 tetrahedral members of about 12-13 Angstroms in diameter. A material having the same structure as VPI-5 is designated MCM-9 and is described in U.S. Pat. No. 4,880,611.

A naturally occurring, highly hydrated basic ferric oxyphosphate mineral, cacoxenite, is reported by Moore and Shen, *Nature*. 306, No. 5941, 356-358 (1983)

to have a framework structure containing very large channels with a calculated free pore diameter of 14.2 Angstroms. R. Szostak et al., *Zeolites: Facts, Figures, Future,* Elsevier Science Publishers B. V. (1989), present work showing cacoxenite as being very hydrophilic, i.e., adsorbing non-polar hydrocarbons only with great difficulty. Their work also shows that thermal treatment of cacoxenite causes an overall decline in X-ray peak intensity.

In layered materials, the interatomic bonding in two directions of the crystalline lattice is substantially different from that in the third direction, resulting in a structure that contains cohesive units resembling sheets. Usually, the bonding between the atoms within these sheets is highly covalent, while adjacent layers are held together by ionic forces or van der Waals interactions. These latter forces can frequently be neutralized by relatively modest chemical means, while the bonding between atoms within the layers remains intact and unaffected.

Certain layered materials, which contain layers capable of being spaced apart with a swelling agent, may be pillared to provide materials having a large degree of porosity. Examples of such layered materials include clays. Such clays may be swollen with water, whereby the layers of the clay are spaced apart by water molecules. Other layered materials are not swellable with water, but may be swollen with certain organic swelling agents such as amines and quaternary ammonium compounds. Examples of such non-water swellable layered materials are described in U.S. Pat. No. 4,859,648 and include trititanates, perovskites and layered silicates, such as magadiite and kenyaite. Another example of a non-water swellable layered material, which can be swollen with certain organic swelling agents, is a vacancy-containing titanometallate material, as described in U.S. Pat. No. 4,831,006.

Once a layered material is swollen, the material may be pillared by interposing a thermally stable substance, such as silica, between the spaced apart layers. The aforementioned U.S. Pat. Nos. 4,831,006 and 4,859,648 describe methods for pillaring the non-water swellable layered materials described therein and are incorporated herein by reference for definition of pillaring and pillared materials.

Other patents teaching pillaring of layered materials and the pillared products include U.S. Pat. Nos. 4,216,188; 4,248,739; 4,176,090 and 4,367,163; and European Patent Application 205,711.

TEMPLATING

In an article by Lok et al., entitled "The Role of Organic Molecules in Molecular Sieve Synthesis", appearing in *Zeolites,* 3, 282-291 (1983), the so-called "templating theory" of molecular sieve synthesis is discussed. According to this theory, individual organic molecular species, such as individual quaternary ammonium ions, may serve as templates about which portions of channels or cages of molecular sieves may form. Although organic molecules would also appear to direct or help the synthesis of certain molecular sieves, such as zeolites and crystalline aluminum phosphates, by influencing the gel chemistry of the reaction mixture, the structures of a number of molecular sieves are consistent with structures derived from reaction mixtures where individual quaternary ammonium ions serve as templates for framework formation.

In most instances, the quaternary ammonium compounds used to synthesize zeolitic molecular sieves do not contain the appropriate features to function as amphiphilic species. Typically, the chain length (R), the "tail" group, is less than six carbons. Therefore, liquid crystal chemistry is not favored in typical zeolite syntheses.

ULTRA-LARGE PORE MATERIALS

U.S. Pat. No. 5,102,643 describes the preparation of various non-layered, ultra-large pore crystalline oxide materials from reaction mixtures containing a solvent, such as water; a source of one or more oxides, such as silica; and an amphiphilic compound, such as a cetyltrimethylammonium compound. The amphiphilic compounds in these reaction mixtures are believed to be in the form of micelles, which, in turn, may be in the form of liquid crystals. These micelles and/or liquid crystals are believed to function as templates for the formation of crystalline oxide frameworks upon crystallization of the reaction mixture.

SUMMARY

There is provided a process for hydrogenating an aromatic compound, said process comprising contacting said aromatic compound and a source of hydrogen under hydrogenation conditions with catalyst comprising a hydrogenation metal and a composition of matter comprising an inorganic, crystalline phase material exhibiting, after calcination, an X-ray diffraction pattern with at least one peak at a position greater than about 18 Angstrom Units d-spacing with a relative intensity of 100, and a benzene adsorption capacity of greater than about 15 grams benzene per 100 grams anhydrous crystal at 50 torr and 25° C. The inorganic, crystalline phase materials in the catalyst may be non-layered materials, e.g., as described in the aforementioned U.S. Pat. No. No. 5,102,643.

EMBODIMENTS

Aromatic compounds which may be hydrogenated in accordance with the present process include monocyclic aromatic compounds and polycyclic aromatic compounds, especially fused ring dicyclic and tricyclic aromatics. Fused ring dicyclic aromatics comprise naphthalene and alkylnapthalenes. Fused ring tricyclic aromatics include anthracene and phenanthrene as well as alkylated derivatives of these. Monocyclic aromatics include benzene and alkylbenzenes.

The present process may be used to produce a saturated cyclic compound, such as cyclohexane, from an aromatic compound, such as benzene. Cyclohexane is an important intermediate chemical for production of Nylon-6, Nylon-66, phenol, and cyclamates. Current worldwide cyclohexane production capacity is about 4.0 MM tons per year. The majority of cyclohexane is produced by direct hydrogenation of benzene.

Toluene may also be saturated by the present process to form methylcyclohexane.

The feedstock to the present process may, optionally, include non-aromatic compounds. The hydrocarbons in this feed may comprise, for example, less than 10 wt.% of non-aromatic hydrocarbons.

Preferred operating conditions are $H_2$/hydrocarbon ratios from 2 to 2000, temperatures from 25° C. to 400° C., pressures from atmospheric to 2000 psig, and liquid hourly space velocities from 0.5 to 200.

The present hydrogenation reaction may take place under conditions such that substantially no side reactions occur. Examples of such side reactions include cracking, dealkylation, transalkylation, isomerization, and ring-opening. The present hydrogenation reaction may take place under conditions sufficient to cause partial or complete saturation of the aromatic compounds.

The crystalline ultra-large pore oxide material described herein may have the following composition:

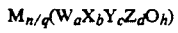
$$M_{n/q}(W_aX_bY_cZ_dO_h)$$

wherein W is a divalent element, such as a divalent first row transition metal, e.g., manganese, cobalt and iron, and/or magnesium, preferably cobalt; X is a trivalent element, such as aluminum, boron, iron, and/or gallium, preferably aluminum; Y is a tetravalent element such as silicon and/or germanium, preferably silicon; Z is a pentavalent element, such as phosphorus; M is one or more ions, such as, for example, ammonium, Group IA, IIA, and VIIB ions, usually hydrogen, sodium and/or fluoride ions; n is the charge of the composition excluding M expressed as oxides; q is the weighted molar average valence of M; n/q is the number of moles or mole fraction of M; a, b, c, and d are mole fractions of W, X, Y, and Z, respectively; h is a number of from 1 to 2.5; and $(a+b+c+d)=1$.

A particular embodiment of the above oxide material is when $(a+b+c)$ is greater than d, and $h=2$. A further embodiment is when a and $d=0$, and $h=2$.

In the as-synthesized form, this material may have a composition, on an anhydrous basis, expressed empirically as follows:

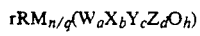
$$rRM_{n/q}(W_aX_bY_cZ_dO_h)$$

wherein R is the total organic material not included in M as an ion, and r is the coefficient for R, i.e., the number of moles or mole fraction of R.

The M and R components are associated with the material as a result of their presence during crystallization and may be removed or, in the case of M, replaced by post-crystallization methods hereinafter more particularly described.

The reaction mixture for preparing crystalline materials described herein may comprise a source of one or more oxides, an amphiphilic compound and water. This amphiphilic compound is also referred to herein as the primary organic agent (R') and is more particularly described hereinafter. Optional components of the reaction mixture include (1) a source of alkali or alkaline earth metal (M), e.g., sodium or potassium, cations; (2) an additional organic agent (R"), hereinafter more particularly described; and (3) an organic swelling agent, also referred to herein as an auxiliary organic agent (R'"), hereinafter more particularly described. Particular sources of oxides include those selected from the group consisting of divalent element W, e.g., cobalt; trivalent element X, e.g., aluminum; tetravalent element Y, e.g., silicon; and pentavalent element, Z, e.g., phosphorus.

The pH of the reaction mixture may be from about 7 to 14, e.g., from about 9 to 14.

The components of the reaction mixture may be combined in any order. In some instances, it may be desired to combine the water and primary organic agent (R') prior to adding the source of oxide to this preformed mixture. Upon the formation of the reaction mixture, this mixture may, optionally, be subjected to an aging step at low temperature, e.g., from about 0 C to about 50° C., for a short period of time, e.g., from about 30 minutes to about 2 hours. This aging step may take place in the presence or absence of agitation of the reaction mixture.

Crystallization of the reaction mixture may take place at elevated temperature, e.g., from about 50° C. to about 200° C, e.g., from about 95° C. to about 150° C., for about 4 to about 90 hours, e.g., from about 16 to about 90 hours. The crystallization may take place under reflux conditions. The crystallization may also take place in the presence of microwave radiation under conditions specified in U.S. Pat. No. 4,778,666.

Batch crystallization of the present crystalline material can be carried out under either static or agitated, e.g., stirred, conditions in a suitable reactor vessel, such as, for example, polypropylene jars or teflon lined or stainless steel autoclaves. Crystallization may also be conducted continuously in suitable equipment. The total useful range of temperatures for crystallization is noted above for each method for a time sufficient for crystallization to occur at the temperature used, e.g., from about 5 minutes to about 14 days. Thereafter, the crystals are separated from the liquid and recovered.

By adjusting conditions of the synthesis reaction for each method, like temperature, pH, and time of reaction, etc., within the above limits, embodiments of the present material with a desired degree of crystallinity or a desired average pore size may be prepared. In particular, changing the pH, the temperature, or the reaction time may promote formation of product crystals with different average pore size.

Non-limiting examples of various combinations of W, X, Y, and Z contemplated for the synthesis methods of the present invention include:

| W  | X  | Y  | Z  |
|----|----|----|----|
| —  | Al | Si | —  |
| —  | Al | —  | P  |
| —  | Al | Si | P  |
| Co | Al | —  | P  |
| Co | Al | Si | P  |
| —  | —  | Si | —  | including the combinations of W being Mg, or an element selected from the divalent first row transition metals, e.g., Mn, Co, and Fe; X being B, Ga, or Fe; and Y being Ge.

A primary organic agent (R') for use in preparing the present reaction mixture may be an ammonium or phosphonium ion of the formula $R_1R_2R_3R_4Q^+$, i.e.:

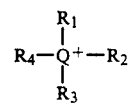

wherein Q is nitrogen or phosphorus and wherein at least one of $R_1$, $R_2$, $R_3$, and $R_4$ is aryl or alkyl or from 6 to about 36 carbon atoms, especially from 8 to 36 carbon atoms, e.g., $-C_{10}H_{21}$, $-C_{16}H_{33}$, and $-C_{18}H_{37}$, or combinations thereof, the remainder of $R_1$, $R_2$, $R_3$, and $R_4$ being selected from the group consisting of hydrogen, alkyl of from 1 to 5 carbon atoms, and combinations thereof. The compound from which the above ammonium or phosphonium ion is derived may be, for example, the hydroxide, halide, silicate, or mixtures thereof.

An additional organic agent (R″) may also be used. That additional organic agent may be the ammonium or phosphonium ion of the above agent formula wherein $R_1$, $R_2$, $R_3$, and $R_4$ together or separately are selected from the group consisting of hydrogen and alkyl of 1 to 5 carbon atoms and combinations thereof. Any such combination of organic agents may be in molar ratio of about 100/1 to about 0.01/1, first above listed organic agent/additional organic agent (R′/R″).

Non-limiting example of R′ capable of forming micelles include cetyltrimethylammonium, cetyltrimethylphosphonium, octadecyltrimethylphosphonium, cetylpyridinium, myristyltrimethylammonium, decyltrimethylammonium, dodecyltrimethylammonium, and dimethyldidodecylammonium.

In addition to the above-mentioned primary organic agent (R′) and the additional organic agent (R″), the reaction mixture may also contain an auxiliary organic agent (R‴). These auxiliary organic agents are compounds which are capable of swelling micelles. Such auxiliary organic agents may be selected from the group consisting of (1) aromatic hydrocarbons and amines having from 5 to 20 carbon atoms and halogen- and $C_1$-$C_{14}$ alkyl-substituted derivatives thereof; (2) cyclic aliphatic hydrocarbons and amines having from 5 to 20 carbon atoms and halogen- and $C_1$-$C_{14}$ alkyl-substituted derivatives thereof; (3) polycyclic aliphatic hydrocarbons and amines having from 6 to 20 carbon atoms and halogen- and $C_1$-$C_{14}$ alkyl-substituted derivatives thereof; (4) straight and branched aliphatic hydrocarbons and amines having from 3 to 16 carbon atoms and halogen-substituted derivatives thereof; and (5) combinations thereof.

In this group of auxiliary organic agents (R‴) for use in the present method, the halogen substituent in substituted derivatives may be, for example, bromine. The $C_1$-$C_{14}$ alkyl substituent in the substituted derivatives may be linear or branched aliphatic chains, such as, for example, methyl, ethyl, propyl, isopropyl, butyl, pentyl, and combinations thereof. Non-limiting examples of these auxiliary organic agents include, for example, p-xylene, trimethylbenzene, triethylbenzene, and triisopropylbenzene. A particular example of such an auxiliary organic agent (R‴) is 1,3,5-trimethylbenzene (i.e., mesitylene).

The mole ratio of the auxiliary organic agent to the primary organic agent (R‴/R′) may be from about 0.02 to about 100, e.g., from about 0.05 to about 35.

The use of auxiliary organic agents in the preparation of certain crystalline ultra-large pore oxide materials is described in U.S. Pat. No. 5,057,296, the entire disclosure of which is expressly incorporated herein by reference.

It should be realized that the reaction mixture components can be supplied by more than one source. The reaction mixture can be prepared either batchwise or continuously. Crystal size and crystallization time of the new crystalline material will vary with the nature of the reaction mixture employed and the crystallization conditions.

The concentration of the amphiphilic compound in the reaction mixture may be such that the molar ratio of amphiphilic compound to water is less than 0.004, e.g., less than 0.002, e.g., less than 0.0015.

In accordance with reactions reported in Examples hereinafter, it has been discovered that the addition of an inorganic salt to a reaction mixture may change the nature of the as-synthesized form of the crystalline material obtained. More particularly, these Examples show that the as-synthesized material may not be thermally stable to calcination conditions, when inorganic salt is omitted from the reaction mixture, whereas a thermally stable as-synthesized material may be obtained when the inorganic salt is added to reaction mixture. Examples of such inorganic salts include alkali metal salts, such as sodium bromide. The concentration of the inorganic salt may be greater than the concentration of the amphiphilic compound, and the former concentration may exceed the latter concentration, e.g., by a factor of 5 or more, e.g., 10 or more.

The oxide material prepared by methods described herein has an X-ray diffraction pattern with at least one peak at a position greater than about 18 Angstrom Units d-spacing with a relative intensity of 100. This pattern may have no peaks at positions less than about 10 Angstrom Units d-spacing with a relative intensity greater than 20% of the strongest peak.

To the extent desired, the original sodium ions of the as-synthesized material described herein can be replaced in accordance with techniques well known in the art, at least in part, by ion exchange with other ions. Examples of such replacing ions include metal ions, hydrogen ions, hydrogen precursor, e.g., ammonium, ions and mixtures thereof. Particular examples of such ions are those which tailor the catalytic activity for certain hydrocarbon conversion reactions. Replacing ions include hydrogen, rare earth metals and metals of Groups IA (e.g., K), IIA (e.g., Ca), VIIA (e.g., Mn), VIIIA (e.g., Ni), IB (e.g., Cu), IIB (e.g., Zn), IIIB (e.g., In), IVB (e.g., Sn), and VIIB (e.g., F) of the Periodic Table of the Elements (Sargent-Welch Scientific Co. Cat. No. S-18806, 1979) and mixtures thereof.

The equilibrium benzene adsorption capacity of this material is measured on the basis of no pore blockage by incidental contaminants. For instance, the sorption test will be conducted on the crystalline material phase having any pore blockage contaminants and water removed by ordinary methods. Water may be removed by dehydration techniques, e.g., thermal treatment. Pore blocking inorganic amorphous materials, e.g., silica, and organics may be removed by contact with acid or base or other chemical agents such that the detrital material will be removed without detrimental effect on the crystal described herein.

In certain Examples which follow, X-ray diffraction data were collected on a Scintag PAD X automated diffraction system employing theta-theta geometry, Cu K-alpha radiation, and an energy dispersive X-ray detector. Use of the energy dispersive X-ray detector eliminated the need for incident or diffracted beam monochromators. Both the incident and diffracted X-ray beams were collimated by double slit incident and diffracted collimation systems. The slit sizes used, starting from the X-ray tube source, were 0.5, 1.0, 0.3 and 0.2 mm, respectively. Different slit systems may produce differing intensities for the peaks. The mesoporous materials described herein that have the largest pore sizes may require more highly collimated incident X-ray beams in order to resolve the low angle peak from the transmitted incident X-ray beam.

The diffraction data were recorded by step-scanning no faster than at 0.04 degrees of two-theta, where theta is the Bragg angle, and a counting time of 10 seconds for each step. The interplanar spacings, d's, were calculated in Angstrom units (A), and the relative intensities of the lines, $I/I_o$, where $I_o$ is one-hundredth of the intensity of the strongest line, above background, were derived with the use of a profile fitting routine. The intensities were uncorrected for Lorentz and polarization effects. The relative intensities are given in terms of the symbols vs=very strong (75-100), s=strong (50-74), m=medium (25-49) and w=weak (0-24). It should be understood that diffraction data listed as single lines may consist of multiple overlapping lines which under certain conditions, such as very high experimental resolution or crystallographic changes, may appear as resolved or partially resolved lines. Typically, crystallographic changes can include minor changes in unit cell parameters and/or a change in crystal symmetry, without a substantial change in structure. These minor effects, including changes in relative intensities, can also occur as a result of differences in cation content, framework composition, nature and degree of pore filling, thermal and/or hydrothermal history, and peak width/shape variations due to particle size/shape effects, structural disorder or other factors known to those skilled in the art of X-ray diffraction.

The equilibrium benzene adsorption capacity may be determined by contacting the crystalline material described herein, after dehydration or calcination at, for example, about 540° C. for at least about one hour and other treatment, if necessary, in an attempt to remove any pore blocking contaminants, at 25° C. and 50 torr benzene until equilibrium is reached. The weight of benzene sorbed is then determined as more particularly described hereinafter.

The present crystalline ultra-large pore oxide materials may have a hexagonal electron diffraction pattern and a hexagonal arrangement of uniformly sized pores. Such are designated as MCM-41, and these materials, as well as the preparation thereof, are described in U.S. Pat. No. 5,098,684, the entire disclosure of which is expressly incorporated herein by reference.

When used as a catalyst component, the crystalline material described herein should be subjected to treatment to remove part or all of any organic constituent. In the present process, the composition is used as a catalyst component (e.g., a support) in intimate combination with a hydrogenating component such as a metal, particularly a transition metal, especially tungsten, vanadium, molybdenum, rhenium, nickel, cobalt, chromium, manganese, or a noble metal such as platinum or palladium. Such component can be in the composition by way of co-crystallization, exchanged into the composition to the extent a Group IIIB element, e.g., aluminum, is in the structure, impregnated therein or intimately physically admixed therewith. Such component can be impregnated in or on to it such as, for example, by, in the case of palladium, treating the material with a solution of a palladium metal-containing ion. Thus, suitable palladium compounds for this purpose include, but are not limited to, palladous chloride and various compounds containing the palladium amine complex such as palladium tetraamine, $Pd(NH_3)_4^{2+}$. In the case of platinum, the material can be treated with a solution containing a platinum metal-containing ion. Suitable platinum compounds for this purpose include, but are not limited to, chloroplatinic acid, platinous chloride and various compounds containing the platinum amine complex, such as platinum tetraamine, $Pt(NH_3)_4^{2+}$.

A preferred technique for combining a hydrogenation component with the present ultra-large pore crystalline phase material is via incipient wetness impregnation.

Incipient wetness impregnation is a technique by which a solution containing either a dissolved or a suspended impregnating agent is used to fill the pores of the solid being treated. The term "incipient wetness" derives from the fact that the amount of liquid used for the impregnation is approximately equivalent to the pore volume of the "bone-dry" solid to be impregnated. In this way, no excess solution remains after the material is treated with the solution, all of the solution having been taken up, via capillary action, by the solid.

An alternative method is termed "excess solution" whereby the solid is saturated (soaked) with an excess amount of solution normally by immersion in a solution containing the impregnant. This technique requires that the solid be blown dry or contacted with an absorbent medium in order to remove the excess liquid and eliminate the "wetness" of the solid.

The above crystalline material, especially in its metal, hydrogen and ammonium forms can be beneficially converted to another form by thermal treatment (calcination). This thermal treatment is generally performed by heating one of these forms at a temperature of at least 400° C. for at least 1 minute and generally not longer than 20 hours, preferably from about 1 to about 10 hours. While subatmospheric pressure can be employed for the thermal treatment, atmospheric pressure is desired for reasons of convenience, such as in air, nitrogen, ammonia, etc. The thermal treatment can be performed at a temperature up to about 750° C. The thermally treated product is particularly useful in the catalysis of certain hydrocarbon conversion reactions.

The crystalline material described herein, when employed either as a support or a catalyst in an organic compound conversion process may be dehydrated, at least partially. This dehydration can be done by heating to a temperature in the range of 200° C. to 595° C. in an atmosphere such as air, nitrogen, etc. and at atmospheric, subatmospheric or superatmospheric pressures for between 30 minutes and 48 hours. Dehydration can also be performed at room temperature merely by placing the composition in a vacuum, but a longer time is required to obtain a sufficient amount of dehydration.

The crystalline ultra-large pore oxide materials can be shaped into a wide variety of particle sizes. Generally speaking, the particles can be in the form of a powder, a granule, or a molded product, such as an extrudate having particle size sufficient to pass through a 2 mesh (Tyler) screen and be retained on a 400 mesh (Tyler) screen. In cases where the catalyst is molded, such as by extrusion, the crystals can be extruded before drying or partially dried and then extruded.

As in the case of many catalysts, it may be desired to incorporate the crystalline ultra-large pore oxide composition with another material resistant to the temperatures and other conditions employed in organic conversion processes. Such materials include active and inactive materials and synthetic or naturally occurring zeolites as well as inorganic materials such as clays, silica and/or metal oxides such as alumina, titania and/or zirconia. The latter may be either naturally occurring or in the form of gelatinous precipitates or gels including mixtures of silica and metal oxides. Use of a material in conjunction with the new crystal, i.e., combined therewith or present during synthesis of the new crystal, which is active, tends to change the conversion and/or selectivity of the catalyst in certain organic conversion processes. Examples of zeolites which may be included in the present catalyst include ZSM-5 and USY. Inactive materials suitably serve as diluents to control the amount of conversion in a given process so that products can be obtained economically and orderly without employing other means for controlling the rate of reaction. These materials may be incorporated with naturally occurring clays, e.g., bentonite and kaolin, to improve the crush strength of the catalyst under commercial operating conditions. Said materials, i.e., clays, oxides, etc., function as binders for the catalyst. It is desirable to provide a catalyst having good crush strength because in commercial use it is desirable to prevent the catalyst from breaking down into powder-like materials. These clay binders have been employed normally only for the purpose of improving the crush strength of the catalyst.

Naturally occurring clays which can be composited with the new crystal include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification.

In addition to the foregoing materials, the crystalline ultra-large pore oxide material can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia.

It may be desirable to provide at least a part of the foregoing matrix materials in colloidal form so as to facilitate extrusion of the bound catalyst components(s).

The relative proportions of finely divided crystalline material and inorganic oxide matrix vary widely, with the crystal content ranging from about 1 to about 90 percent by weight and more usually, particularly when the composite is prepared in the form of beads, in the range of about 2 to about 80 weight percent of the composite.

In order to more fully illustrate the nature of the invention and the manner of practicing same, the following Examples are presented. In the Examples, whenever sorption data are set forth for comparison of sorptive capacities for water, cyclohexane, benzene and/or n-hexane, they are Equilibrium Adsorption values determined as follows:

A weighed sample of the adsorbent, after calcination at about 540° C. for at least about 1 hour and other treatment, if necessary, to remove any pore blocking contaminants, is contacted with the desired pure adsorbate vapor in an adsorption chamber. The increase in weight of the adsorbent is calculated as the adsorption capacity of the sample in terms of grams/100 grams adsorbent based on adsorbent weight after calcination at about 540° C.. The present composition may exhibit an equilibrium benzene adsorption capacity at 50 Torr and 25° C. of greater than about 10 grams/100 grams, e.g., greater than about 12.5 g/100 g, e.g., greater than about 15 grams/100 grams, e.g., greater than about 17.5 g/100 g, e.g., greater than about 20 g/100 g, e.g., greater than about 30 g/100 g.

A preferred way to do this is to contact the desired pure adsorbate vapor in an adsorption chamber evacuated to less than 1 mm at conditions of 12 Torr of water vapor, 40 Torr of n-hexane or cyclohexane vapor, or 50 Torr of benzene vapor, at 25° C. The pressure is kept constant (within about ±0.5 mm) by addition of adsorbate vapor controlled by a manostat during the adsorption period. As adsorbate is adsorbed by the new crystal, the decrease in pressure causes the manostat to open a valve which admits more adsorbate vapor to the chamber to restore the above control pressures. Sorption is complete when the pressure change is not sufficient to activate the manostat.

Another way of doing this for benzene adsorption data is on a suitable thermogravimetric analysis system, such as a computer-controlled 990/951 duPont TG system. The adsorbent sample is dehydrated (physically sorbed water removed) by heating at, for example, about 350° C. or 500° C. to constant weight in flowing helium. If the sample is in as-synthesized form, e.g., containing organic agents, it is calcined at about 540° C. in air and held to constant weight instead of the previously described 350° C. or 500° C. treatment. Benzene adsorption isotherms are measured at 25° C. by blending a benzene saturated helium gas stream with a pure helium gas stream in the proper proportions to obtain the desired benzene partial pressure. The value of the adsorption at 50 Torr of benzene is taken from a plot of the adsorption isotherm.

In the Examples, percentages are by weight unless otherwise indicated.

EXAMPLE 1

Sixty-one parts by weight of a 29 wt.% cetyltrimethylammonium hydroxide solution were charged to an autoclave together with 30 parts by weight of a 10 wt.% tetramethylammonium silicate solution, 7.6 parts by weight of a precipitated silica (tradename HiSil) and 1.4 parts by weight of sodium aluminate. The resulting pH was 12.6. The mixture was stirred and then heated to 100° C. and held at this temperature for 24 hours under autogeneous pressure. The crystallized product was filtered and washed overnight with DI water. The calcined product had the following properties:

| Surface area, $m^2$,g | 1102 |
|---|---|
| Sorption Capacity, wt. % | |
| n-$C_6$ @ 40 Torr | 48.3 |
| Cy$C_6$ @ 40 Torr | 50.0 |
| $H_2O$ @ 12 Torr | 11.7 |
| Sodium, ppm | 1240 |
| $SiO_2$, wt. % | 94.8 |
| $Al_2O_3$, wt. % | 5.2 |
| $SiO_2/Al_2O_3$ (molar) | 31.0 |

The product of this Example is designated as MCM-41 in the Examples which follow.

EXAMPLE 2

A typical Pd MCM-41/$Al_2O_3$ catalyst was prepared as follows. A sample of the as-synthesized MCM-41 from Example 1 was ammonium exchanged and dried at 250° F. overnight. The sample was extruded with alumina. After being calcined in $N_2$ for 6 hrs. and air for 12 hrs., the sample was prepared by incipient wetness impregnation of Pd(NH$_3$)$_4$Cl$_2$ (~1 wt.% Pd). The final calcination was performed at 550° F. (288° C.) in air for 3 hrs.

EXAMPLES 3

Samples prepared from Example 2 were tested for benzene (Bz) hydrogenation activity. Tests were performed at 100° C., atm pressure, $pH_2=730$ Torr, $pBz=30$ Torr, and $WHSV=5$ hr$^{-1}$. The $H_2$/benzene mole ratio was 100:1. Table 1 shows the result on benzene hydrogenation activity of two Pd MCM-41/Al$_2$O$_3$ samples. Other Pd samples were included for comparison.

Table 2 compares catalyst properties of Pd MCM-41/Al$_2$O$_3$ and Pd/SiO$_2$. MCM-41/Al$_2$O$_3$ catalyst shows higher surface area and pore volume. Results of chemisorption of hydrogen and oxygen indicate that the MCM-41/Al$_2$O$_3$ catalyst gives higher dispersion of palladium. More importantly, pore size distributions are significantly different. About one third of pore volume of the MCM-41/Al$_2$O$_3$ catalyst has pore diameters less than 50 Angstroms.

TABLE 1

Benzene Hydrogenation Activity of Pd Catalysts

| Catalyst | Rate Constant @ 100° C. Mole Benzene Mole Metal/Hour |
|---|---|
| Pd MCM-41/Al$_2$O$_3$ | 55.8 |
| Pd MCM-41/Al$_2$O$_3$ | 48.2 |
| Pd USY | 8.7 |
| Pd ZSM-5 | 30.1 |
| Pd ZSM-23/Al$_2$O$_3$ | 8.7 |
| Pd SiO$_2$ | 15.0 |

TABLE 2

Catalyst Properties

| Catalyst | Pd MCM-41[1] | Pd SiO$_2$ |
|---|---|---|
| Metal Loading, wt. % | | |
| Pd | 0.83 | 0.84 |
| Chemisorption[2] | | |
| H/Pd | 1.06 | 0.71 |
| O/Pd | 0.52 | 0.18 |
| Surface Area, m$^2$/g | 800 | 330 |
| Pore Volume, cc/g | 0.96 | 0.88 |
| Pore Distribution, % | | |
| <50 A | 32 | 0 |
| 50-100 A | 16 | 41 |
| 100-200 A | 15 | 32 |
| >200 A | 37 | 37 |

[1]Contains 65 wt. % MCM-41 and 35 wt. % alumina prior to the metal addition
[2]Atomic ratio

What is claimed is:

1. A process for hydrogenating an aromatic compound, said process comprising contacting said aromatic compound and a source of hydrogen under hydrogenation conditions with catalyst comprising a hydrogenation metal in intimate combination with a composition of matter comprising an inorganic, crystalline phase material exhibiting, after calcination, an X-ray diffraction pattern with at least one peak at a position greater than about 18 Angstrom Units d-spacing with a relative intensity of 100, and a benzene adsorption capacity of greater than about 15 grams benzene per 100 grams anhydrous crystal at 50 torr and 25° C.

2. A process according to claim 1, wherein said hydrogenating metal is platinum or palladium.

3. A process according to claim 1, wherein said hydrogenating metal is palladium.

4. A process according to claim 1, wherein said catalyst further comprises a binder.

5. A process according to claim 4, wherein said binder is alumina.

6. A process according to claim 1, wherein said aromatic compound is a monocyclic aromatic compound.

7. A process according to claim 6, wherein said monocyclic aromatic compound is benzene or toluene.

8. A process according to claim 1, wherein benzene is hydrogenated to form cyclohexane.

9. A process according to claim 1, wherein said inorganic, crystalline phase material is a non-layered material.

10. A process according to claim 1, wherein the crystalline material has, after calcination, an arrangement of uniformly-sized pores having diameters of at least about 13 Angstrom Units.

11. A process according to claim 1, wherein the crystalline phase has a hexagonal arrangement of uniformly-sized pores of at least 13 Angstroms diameter and which exhibits, after calcination, a hexagonal electron diffraction pattern that can be indexed with a d100 value greater than about 18 Angstroms.

12. A process according to claim 11, wherein the crystalline phase has, after calcination, an X-ray diffraction pattern which exhibits at least two peaks at positions greater than about 10 Angstrom Units d-spacing, at least one of which is at a position greater than about 18 Angstrom Units d-spacing, and no peaks at positions less than about 10 Angstrom Units d-spacing with relative intensity greater than about 20% of the strongest peak.

13. A process according to claim 11, wherein the crystalline phase has, after calcination, an X-ray diffraction pattern which exhibits no peaks at positions less than about 10 Angstrom Units d-spacing with relative intensity greater than about 10% of the strongest peak.

14. A process according to claim 1, wherein the crystalline material is a silicate.

15. A process according to claim 1, wherein the crystalline material is an aluminosilicate.

16. A process according to claim 1, wherein the catalyst further comprises a zeolite selected from the group consisting of ZSM-5 and USY.

* * * * *